(12) United States Patent
Schaeffer (10) Patent No.: US 10,314,704 B2
(45) Date of Patent: Jun. 11, 2019

(54) ARTIFICIAL DEVICE DEPLOYMENT APPARATUS

(71) Applicant: Cook Medical Technologies LLC, Bloomington, IN (US)

(72) Inventor: Darin G. Schaeffer, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1064 days.

(21) Appl. No.: 14/453,127

(22) Filed: Aug. 6, 2014

(65) Prior Publication Data

US 2014/0350661 A1 Nov. 27, 2014

Related U.S. Application Data

(63) Continuation of application No. PCT/US2013/024891, filed on Feb. 6, 2013.

(60) Provisional application No. 61/595,306, filed on Feb. 6, 2012.

(51) Int. Cl.
*A61F 2/24* (2006.01)
*A61F 2/06* (2013.01)
*A61F 2/848* (2013.01)
*A61F 2/01* (2006.01)

(52) U.S. Cl.
CPC ............. *A61F 2/2436* (2013.01); *A61F 2/06* (2013.01); *A61F 2/2412* (2013.01); *A61F 2/2475* (2013.01); *A61F 2/848* (2013.01); *A61F 2002/011* (2013.01); *A61F 2002/8483* (2013.01)

(58) Field of Classification Search
CPC ........ A61F 2002/011; A61F 2002/8483; A61F 2/848; A61F 2/2475; A61F 2220/0016; A61F 2/2427; A61B 17/0401
USPC ........................................................ 606/200
See application file for complete search history.

(56) References Cited

U.S. PATENT DOCUMENTS

| | | | |
|---|---|---|---|
| 6,602,286 B1 * | 8/2003 | Strecker | A61F 2/2412 623/1.24 |
| 2003/0191525 A1 * | 10/2003 | Thornton | A61F 2/2412 623/1.24 |
| 2004/0138682 A1 * | 7/2004 | Onuki | A61B 17/0401 606/144 |
| 2008/0294001 A1 * | 11/2008 | Surti | A61B 17/0057 600/104 |

* cited by examiner

*Primary Examiner* — Diane D Yabut
*Assistant Examiner* — Majid Jamialahmadi
(74) *Attorney, Agent, or Firm* — Woodard, Emhardt, Henry, Reeves and Wagner LLP (57) ABSTRACT

Described, in certain aspects of the invention, are apparatuses and methods for deploying artificial devices within the vascular system. One apparatus includes a delivery device having a lumen and a deployment member slidably received within the lumen. This apparatus further includes an artificial device having an anchoring element releasably engaged with the deployment member. Such an apparatus can be percutaneously delivered to a site within a vascular vessel, and thereafter manipulated so that the anchoring element attaches to the vessel wall. The delivery device and deployment member can then be withdrawn from the vessel, whereby the deployment member disengages from the anchoring element, leaving the artificial device implanted in the vessel.

19 Claims, 8 Drawing Sheets

ARTIFICIAL DEVICE DEPLOYMENT APPARATUS

REFERENCE TO RELATED APPLICATION

This application is a continuation and claims the benefit of priority of International Application Serial No. PCT/US2013/024891, filed Feb. 6, 2013, which claims the benefit of priority of U.S. Provisional Patent Application Ser. No. 61/595,306 filed Feb. 6, 2012, each of which is hereby incorporated herein by reference in its entirety.

BACKGROUND

The present invention resides generally in the field of medical technology and more particularly relates to apparatuses and methods for deploying medical implants, especially frameless valves, within the vascular system.

It is well understood in human pathology that the proper functioning of cardiac and venous valves is of the utmost importance. Numerous studies have shown that diseased cardiac valves cause significant morbidity and mortality and that incompetent or destroyed venous valves often result in adverse medical conditions, especially in the lower extremities.

By preventing retrograde blood flow, the valves found throughout the venous system assist the flow of blood through the veins and returning to the heart. Venous valves are usually of the bicuspid type, with each cusp or leaflet forming a reservoir for blood, which, under pressure, forces the free edges of the cusps together to permit mostly antegrade blood flow to the heart. As a majority of venous blood flow is against gravity while a person is standing, incompetent or destroyed venous valves can cause significant medical problems in the legs, ankles, and feet. There are at least two chronic venous diseases in which venous valve incompetence is thought to be an important factor: chronic venous insufficiency and varicose vein syndrome.

Chronic venous insufficiency involves venous hypertension and chronic venous stasis due to valvular incompetence. It has been estimated that in the United States chronic venous insufficiency associated with skin changes and ulcers affects six to seven million people. Varicose vein syndrome involves vein dilation or enlargement. According to another estimate, varicose veins affect about 4% of the adult western population, and approximately half of this population has significant varicose vein syndrome for which treatment will be sought.

Turning now to the cardiovascular system, incompetent or destroyed heart valves are a common form of heart disease, the leading cause of death in the United States. Although reconstructive surgery has been shown to be superior to valve replacement surgery in some respects, it is difficult to perform and not always possible in every patient. As a result, the vast majority of patients with diseased heart valves undergo valve replacement surgery, which involves removing a native valve and replacing it with a prosthetic one. Prosthetic heart valves come in various shapes and sizes and can be formed with a variety of materials. Often, the design of a prosthetic valve depends on the characteristics of the valve being replaced (e.g., mitral, aortic, tricuspid, or pulmonary) and/or the size of the patient's heart.

To treat a condition of the vascular system, it may be desirable to deploy an artificial device, such as a valve, within a vascular vessel. Accordingly, a variety of artificial valves have been developed in the art for implantation within the vasculature. Likewise, a variety of delivery apparatuses and methods have been developed for deploying these and other devices. For example, U.S. Pat. No. 6,508,833 discloses a multiple-sided medical device that is pushed from a delivery catheter into the lumen of a duct or vessel, the device comprising a closed frame of a single piece of wire or other resilient material and having a series of bends and interconnecting sides. The device has both a flat configuration and a second, folded configuration that comprises a self-expanding frame. A covering of fabric or other flexible material is sutured or attached to the frame to form an artificial valve. The flexible material utilized in the disclosed valves can be comprised of collagenous submucosa obtained from various animals, such as, for example, pigs, cattle, and sheep. The submucosal material can be prepared in large, flat sheets, which are subsequently cut and attached to a framing element, for example a stent, for deployment in a vein.

There remain needs for improved and/or alternative apparatuses and methods for deploying artificial devices, and in particular frameless valves, within the vasculature. Advantageous deployment apparatuses would include at least one deployment member releasably engaged with at least one anchoring element. Advantageous deployment methods would effectively and efficiently deploy an artificial device. The present invention is addressed to those needs.

SUMMARY

In one embodiment, the present invention provides an apparatus for deploying an artificial implant device within a vascular vessel. This particular apparatus includes a delivery device having a lumen, and at least one elongate deployment member slidably received within the lumen. Preferred delivery devices include percutaneously advancable devices such as catheters. The apparatus further includes an artificial implant device having at least one anchoring element for anchoring the device to walls of the vessel. The at least one anchoring element is releasably engaged with the at least one deployment member. A deployment member can be configured to receive at least a portion of an artificial implant device and/or portions of one or more anchoring elements. Suitable anchoring elements can include, for example, resorbable or non-resorbable barbs. In preferred apparatuses, the artificial implant device comprises a frameless valve formed with a flexible material and in particular a remodelable material, such as but not limited to a remodelable extracellular matrix material. In some forms, the at least one anchoring element is releasably engaged with the at least one elongate deployment member with a removable component, e.g., a suture.

In yet another embodiment, the invention provides a method that includes percutaneously delivering at least one anchoring element and at least one deployment member to a site within a vascular vessel, wherein the at least one anchoring element is releasably engaged with the at least one deployment member. This releasable engagement can be accomplished in any suitable manner, for example, by releasably bonding or suturing, force fitting, and the like. The method further includes percutaneously attaching the at least one anchoring element to a vessel wall. In certain aspects, percutaneously attaching comprises manipulating the at least one deployment member, for example, distally sliding the same within the vessel to force the at least one anchoring element to embed within or penetrate through the wall. Still further, the method includes withdrawing the at least one deployment member from the vessel, whereby the at least one anchoring element remains attached to the vessel wall. In preferred aspects, the at least one anchoring element incorporates or is attached to an artificial implant device and in particular a frameless valve, wherein the frameless valve can be formed with submucosa. Also, the at least one deployment member can be curved, bent, or otherwise suitably configured to facilitate deployment of the artificial implant device.

In another embodiment, the present invention provides an apparatus for attaching at least one anchoring element to a wall of a vascular vessel. The apparatus comprises a delivery device having at least one deployment member passageway therethrough, and at least one deployment member slidably received within the at least one passageway. The apparatus further comprises at least one anchoring element releasably engaged with the at least one deployment member. In preferred aspects, the apparatus includes at least one valve leaflet attached to the at least one anchoring element.

Other objects, embodiments, forms, features, advantages, aspects, and benefits of the present invention shall become apparent from the detailed description and drawings included herein.

DETAILED DESCRIPTION

While the present invention may be embodied in many different forms, for the purpose of promoting an understanding of the principles of the present invention, reference will now be made to the embodiments illustrated in the drawings, and specific language will be used to describe the same. It will nevertheless be understood that no limitation of the scope of the invention is thereby intended. Any alterations and further modifications in the described embodiments and any further applications of the principles of the present invention as described herein are contemplated as would normally occur to one skilled in the art to which the invention relates.

As disclosed above, the present invention in some aspects provides apparatuses, systems, and methods for deploying implantable devices within the vascular system to modify blood flow. In just one embodiment, the invention provides an apparatus for implanting or engrafting a prosthetic valve in a vein to treat venous insufficiency.

Provided below are descriptions of certain embodiments of the invention. It will be understood that the embodiments described below include various features and that absent an indication or operational conflict otherwise, these features, either individually or in combination with other features of the embodiments described below, can be combined with the features of embodiments generally described in the Summary above to provide additional disclosed embodiments herein.

Figure 1:
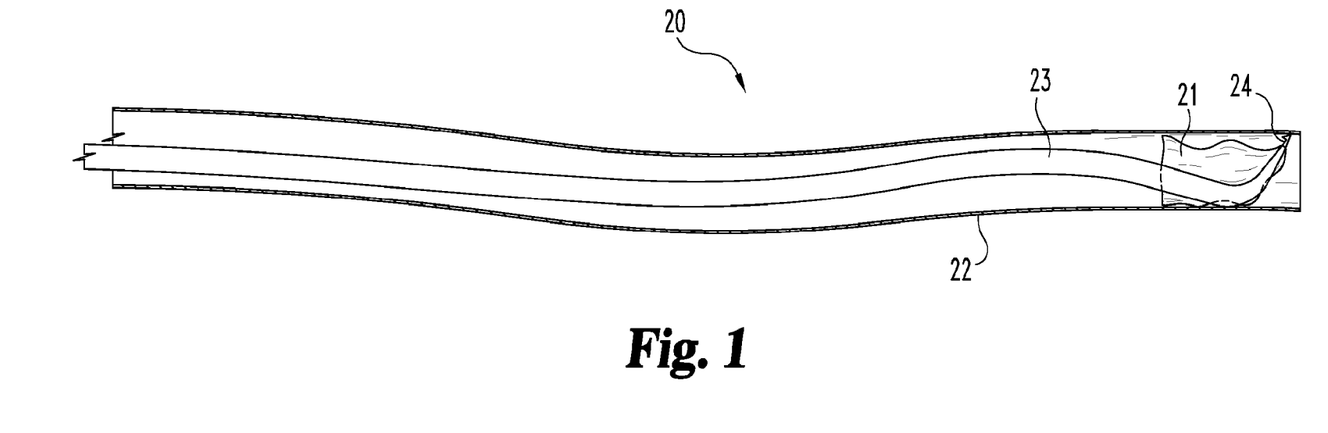
FIG. 1 provides a front view of an apparatus of the present invention.

With reference now to FIGS. 1 and 2A through 2C together, shown in FIG. 1 is an illustrative apparatus 20 of the present invention for deploying an artificial implant device 21 within a vascular vessel. The apparatus 20 generally includes a delivery device 22 having a lumen. It also includes a first elongate deployment member 23 that is slidably received within the lumen. The first deployment member is releasably engaged with a first anchoring element 24. The anchoring element is attached to or incorporated into the artificial implant device 21, and is configured to attach the artificial implant device 21 to a vessel wall. An illustrative deployment of artificial implant device 21 using apparatus 20 is described below in relation to FIGS. 2A through 2C.

While FIG. 1 shows a single deployment member, it should nevertheless be understood that apparatuses having any suitable number of deployment members, e.g., one, two, three, four, or more deployment members, are contemplated as within the scope of the present invention. Illustratively, one such embodiment is depicted in FIG. 2C. Also, while the deployment member depicted in FIG. 1 is releasably engaged with a corresponding anchoring element, other embodiments of the invention cover apparatuses having one or more deployment members, wherein each deployment member can be releasably engaged with any suitable number of anchoring elements. Further, a deployment member can have any suitable size, shape, and/or configuration to facilitate deployment of an artificial implant device (or multiple devices) within a vascular vessel.

The artificial implant device 21 depicted in FIG. 1 comprises a segment of flexible material such as a valve leaflet. However, it should be understood that an artificial implant device of the present invention can comprise any object that is suitable for implantation or deployment within the vascular system, including but not limited to a valve, stent, occluder or other implantable prosthesis or device. Also, the flexibility of an artificial implant device of the invention can vary, wherein different degrees of flexibility can be designed through routine experimentation so as to allow for an optimal degree of flexibility for a given application, procedure, technique, or patient. In this regard, the artificial implant device 21 is semi-rigid in certain embodiments. In other embodiments, the artificial implant device 21 comprises one or more valves to selectively restrict the flow of blood through a vascular vessel, e.g., a vein. In these embodiments, the valves are preferably frameless, although the deployment of valves having a support structure are contemplated as within the scope of the present invention. Support structures, e.g. frames, commonly exert significant radial force upon vessel walls, and in certain situations may migrate deleteriously into the walls and/or undesirably reduce the compliancy of the vessel in which they are implanted. As well, such frame structures can present increased risks for thrombosis or embolism.

Further in this regard, the artificial implant device 21 can have any suitable size, shape, and/or configuration for vascular implantation, and can be designed for temporary or permanent deployment. Also, the artificial implant device 21 can be formed with any suitable biocompatible material, including but not limited to a remodelable material and/or a synthetic polymeric material. In preferred embodiments, the artificial implant device 21 comprises a remodelable extracellular matrix (ECM) material, such as but not limited to small intestinal submucosa (SIS).

The first anchoring element 24 is configured to at least help hold the flexible material 21 at a general location within the vessel. Therefore, while portions of the flexible material 21 may be adapted to move within the vessel to perform a particular function, e.g., a valving function, the anchoring element generally helps prevent the flexible material as a whole from migrating from the implantation site. While the anchoring element 24 illustrated in FIG. 1 is a barb, it will nevertheless be understood that an anchoring element of the present invention can comprise any object, device, or material suitable to attach one of the artificial implant devices disclosed herein to a vessel wall. For example, in certain embodiments, an anchoring element incorporates an adhesive, while in other embodiments, an anchoring element comprises one or more tissue-penetrating attachment elements, such as but not limited to hooks, microbarbs, spurs, claws, prongs, and the like. Also, the present invention provides for artificial implant devices having any suitable number of anchoring elements, e.g., one, two, three, four, or more anchoring elements such as ten to twenty anchoring elements.

Further in this regard, it will be understood that an anchoring element can have a variety of sizes, orientations, and/or shapes to effectively attach the artificial implant device to a vessel wall. For example, an anchoring element can adopt a curved configuration and/or can have adaptations to cause it to resist withdrawal from the wall tissue once inserted therein, e.g. in the case of fish hook-type structures. Similarly, an anchoring element of the invention can be formed with any suitable biocompatible material, and in some embodiments is formed with a bioresorbable material. In other embodiments, one or more anchoring elements and an artificial implant device are formed with the same material. In these embodiments, an anchoring element and an artificial implant device can be formed from separate pieces of material, or portions of the artificial implant device can be manipulated in some manner, such as but not limited to cross linking, freeze drying, and the like, to form one or more anchoring elements therein.

Alternatively, an anchoring element can be formed with a material different than that of an artificial implant device such as device 21. For example, in certain embodiments, an anchoring element is formed with a rigid or semi-rigid synthetic polymeric material, including but not limited to polytetrafluoroethylene (PTFE) (including expanded PTFE) and/or polyethylene terephthalate (PET). In other embodiments, an anchoring element is formed with a rigid or semi-rigid metallic material, including but not limited to, stainless steel, titanium, cobalt, tantalum, gold, platinum, nickel, iron, copper and the like, as well as alloys of these metals (e.g., cobalt alloys, such as Elgiloy®, a cobalt-chromium-nickel alloy, MP35N, a nickel-cobalt-chromium-molybdenum alloy, and Nitinol®, a nickel-titanium alloy). In still other embodiments, an anchoring element is formed with an appropriate ceramic material, including, without limitation, hydroxyapatite, alumina and pyrolytic carbon. Further in this regard, an anchoring element can include a radiopaque material for positioning and monitoring the artificial implant device within the vessel.

In the illustrative embodiment, an adhesive secures the barb 24 to the segment of flexible material 21. However, it should be understood that the barb could be attached to the segment of material 21 in any suitable manner, including but not limited to suturing, stapling, bolting, riveting, gluing, welding, and the like. Also, in some embodiments, a barb or other similar anchoring element incorporates one or more eyelets, plates, and the like for attachment directly to an artificial implant device, e.g., by sewing.

Figure 2A:
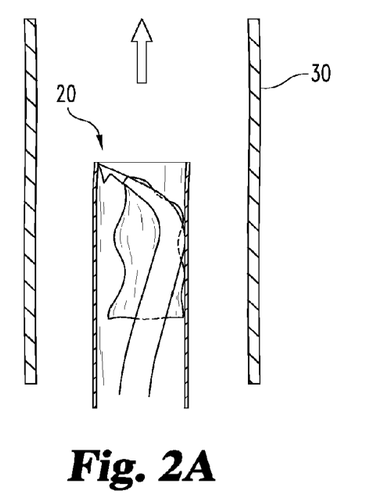
FIGS. 2A, 2B and 2C provide illustrations of the apparatus of FIG. 1 being used to deploy an artificial device within a vascular vessel.
Figure 2B:
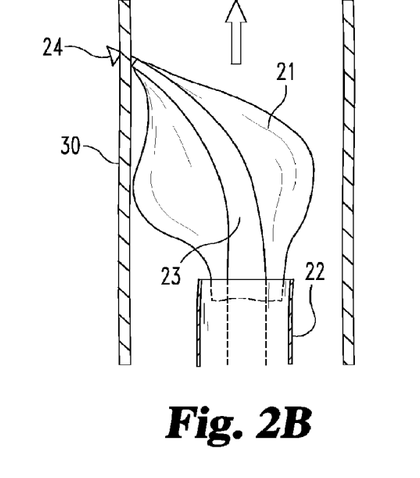
Figure 2C:
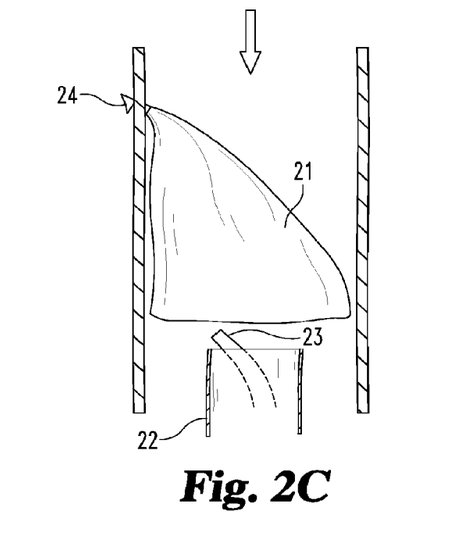

FIGS. 2A through 2C illustrate apparatus 20 being used to deploy artificial implant device 21 within a vascular vessel, e.g., a vein. Referring first to FIG. 2A, one phase of the illustrative deployment includes percutaneously advancing the apparatus 20 (in the direction of the arrow) to a site within the vessel, e.g. a treatment site. While the illustrative delivery device 22 comprises a catheter, it should be understood that a delivery device of the present invention can comprise any device or object suitable for percutaneously delivering at least one of the artificial implant devices and at least one of the deployment members of the present invention to a site within a vascular vessel. Further, the catheter 22 can be delivered to the treatment site using any suitable delivery technique, such as but not limited to tracking an emplaced guidewire with the lumen.

Referring now to FIG. 2B, shown is another phase of the illustrative deployment, wherein the first deployment member 23 is manipulated to attach the first barb 24 to the vessel wall 30. This phase of the deployment is generally achieved by holding the catheter 22 in a fixed position and pushing the first deployment member 23 generally in the direction of the arrow until the first barb 24 penetrates the vessel tissue. If present, any additional deployment member and its respective anchoring element(s) can remain within the catheter 22 during this phase.

By contacting the barb directly, the deployment member is configured to exert force on its respective barb rather than the segment of flexible material 21 during attachment of the barb to the vessel wall 30. Also, the distal ends of the first deployment member 23 is suitably curved to guide the barb toward the vessel wall 30 as the deployment member is advanced distally. Various deployment member shapes can be designed through routine experimentation so as to allow for optimal placement of a barb. Moreover, the first deployment member 23 can be further manipulated to adjust or alter the orientation of its respective barb after the barb initially penetrates the vessel wall 30.

Continuing with FIG. 2B, during this phase of the illustrative deployment, the first barb 24 is releasably engaged with the first deployment member 23, while being simultaneously attached to the vessel wall 30. As depicted, portions of the barb 24 are sticking out of opposite side of the vessel wall 30. However, it should be understood that a barb or other anchoring element of the present invention can embed within or partially or wholly penetrate a vessel wall.

With reference now to FIG. 2C, shown is an alternative embodiment of the apparatus which incorporates a second elongate deployment member 25 and a third elongate deployment member 27 which are releasably engaged with a second anchoring element 26 and a third anchoring element 28, respectively. Here, the segment of material 21 has been fully pushed from the catheter 22. During this phase of the deployment, the second and third deployment members 25 and 27 are manipulated as generally described above to attach the second and third barbs 26 and 28, respectively, to the vessel wall 30. Also, the first deployment member 23 is pulled in the direction of the arrow until it disengages from the first barb 24. In the illustrative embodiment, the barbs are releasably engaged with the deployment members in a way that allows the barbs to remain attached to the vessel wall 30 but disengage from the deployment members when a force within a certain range is applied.

The barbs and deployment members of the invention can be releasably engaged in any suitable manner. For example, the barbs and deployment members can be releasably glued or force fitted together, or the barbs and/or deployment members can incorporate a releasable device, object, or material such as a releasable suture or adhesive. Illustratively, a deployment member can include a distal tip that is cupped by and releasably engaged with an anchoring element that is releasable from the distal tip when a sufficient retraction force is applied to the deployment member. In some forms, the deployment member will define a cavity that receives a post or other projection of the barb or other anchoring element. The post snugly fits into the cavity (e.g., by force fitting) and is releasable therefrom when the barb is embedded in the vessel wall and the deployment member is retracted. Such a post can include further features to aid in its temporary retention in the deployment member cavity such as a ball or other lateral projection off the post that enhances its retention capabilities in the cavity. Although not shown in FIG. 2C, once the first, second, and third deployment members 23, 25, and 27 disengage from their respective barbs, the deployment members and catheter can be removed from the patient, whereby the segment of material 21 remains deployed within the patient's vessel to modify the flow of blood. However, it should be understood that when a plurality of deployment members are involved, they can be manipulated and/or withdrawn in any order.

Figure 3:
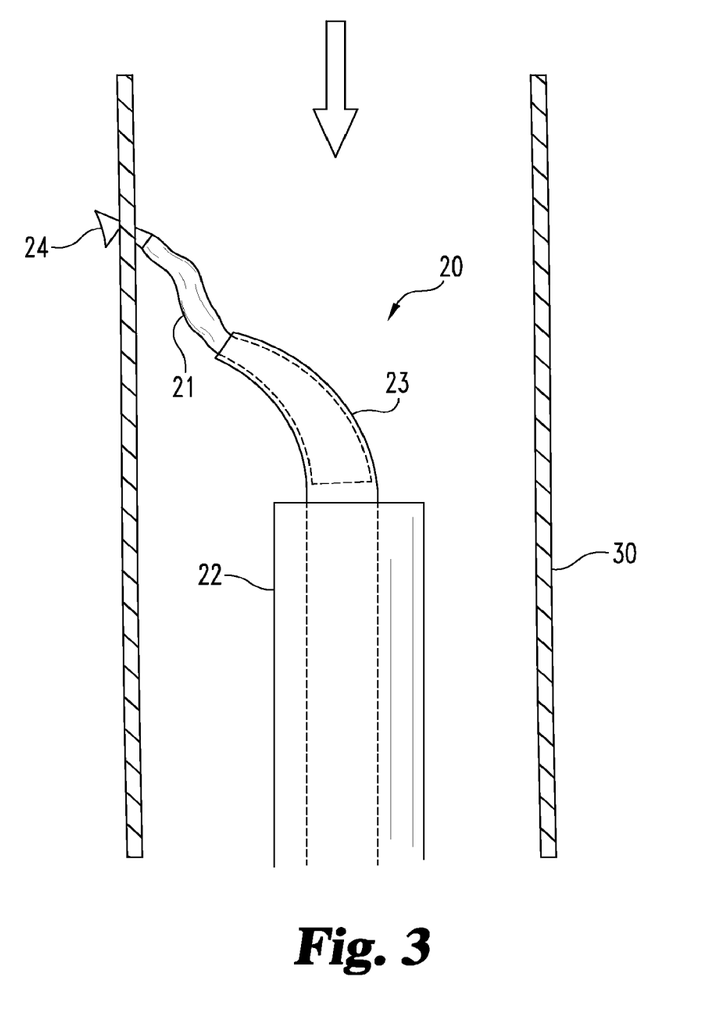
FIG. 3 provides a front view of an apparatus of the present invention, wherein an artificial device is received within a lumen of a deployment member.

FIG. 3 provides an illustrative use of an alternative embodiment of apparatus 20. This apparatus embodiment is similar to that shown in FIG. 1 except in respect of the configuration of the deployment member and the segment of flexible material 21. Whereas the segment of material of FIG. 1 is positioned alongside the deployment members in the delivery device, the segment of material of the current embodiment is receivable within a lumen of the first deployment member 23. In this illustration, the segment of material 21 is being pulled through the distal end of the first deployment member lumen as the first deployment member 23 is being retracted in the direction of the arrow (following its disengagement from the first anchoring element 24). The first anchoring element 24 is attached to a vessel wall 30. Optionally, additional deployment members such as the second and third deployment members 25 and 27 (and their respective anchoring elements) from FIG. 2C can be received within the lumen of the first deployment member 23, and can be manipulated (e.g. pushed therefrom) to attach the additional barbs or other anchoring elements to the vessel wall 30.

Receiving all or part of the artificial implant device 21 within the deployment member 23 can reduce the risk of damaging the artificial implant device 21 during a deployment procedure. Moreover, such a configuration (i.e., having all or part of an artificial implant device and/or one or more deployment members received within a deployment member) may permit use of a smaller delivery device 22 or eliminate the need for a delivery device altogether.

Figure 4A:
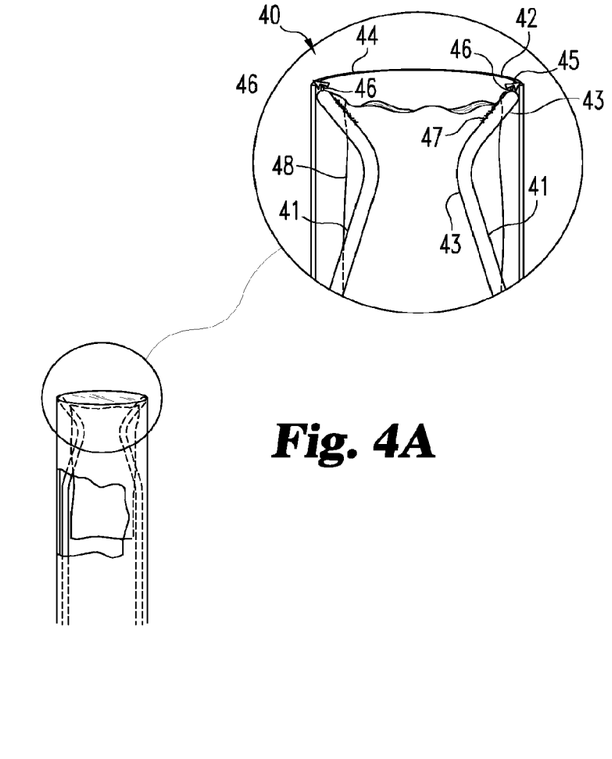
FIG. 4A provides a perspective view of another apparatus of the present invention.

FIG. 4A provides a perspective view of another apparatus 40 of the present invention, which includes a pair of elongate deployment members 41 slidably received within a lumen of a delivery device 42 such as a catheter. The deployment members 41 generally include curved portions 43, which facilitate the distal ends of the deployment members moving outwardly toward the vessel walls upon exiting the distal end 44 of the catheter 42. Each deployment member 41 is releasably engaged with a corresponding hook 45 or other suitable vessel-attaching element via engagement adaptations 46. In the illustrated embodiment, the engagement adaptations 46 may be part of the hook, deployment member, or both. Further, sutures 47 attach the hooks 45 to one end of an artificial implant device 48, which in the illustrative embodiment comprises a frameless tube formed with a remodelable extracellular (ECM) material.

Figure 4B:
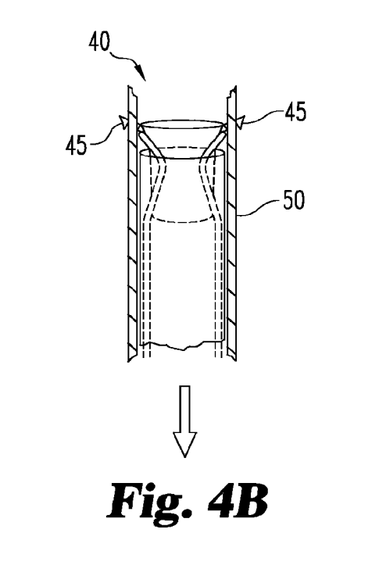
FIGS. 4B and 4C provide illustrations of the apparatus of FIG. 4A being used to deploy a tubular device within a bodily passageway.
Figure 4C:
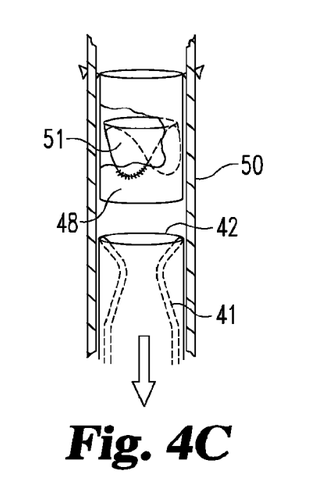

FIGS. 4B and 4C illustrate apparatus 40 being used to deploy tube 48 within a bodily passageway, e.g., a vascular vessel. Referring first to FIG. 4B, shown is the apparatus 40 after the hooks 45 have exited the distal end 44 of the catheter 42 (on the distal ends of the deployment members 41) and penetrated at least partially through walls 50 of the vessel. This phase of the illustrative deployment is generally achieved by holding the deployment members 41 in a fixed position and sliding the catheter 42 over the deployment members in the direction of the arrow. The hooks 45 are driven into the vessel tissue 50 by the distal ends of the semi-flexible deployment members 41, which are configured to move away from each other and toward the vessel walls 50 upon exiting the catheter 42. In this regard, the deployment members 41 can have various shapes and configurations to optimize the degree of advancement of the hooks 45 toward the vessel walls and/or the force applied to the hooks 45 as they penetrate the vessel tissue 50. In certain embodiments, a spring or spring-like adaptation is incorporated into or attached to the deployment members to facilitate deployment of an artificial implant device. In certain other embodiments, the deployment members themselves can be spring-like. In these embodiments, the deployment members can be compressed inwardly (i.e., toward each other) when inside the catheter so that they spring outwardly (i.e., away from each other) when pushed out of the catheter. In still further embodiments, the deployment members and/or delivery device incorporates a mechanism or device that forces the deployment members to move away from each other when manipulated in a particular manner (e.g., when advanced out of or toward the distal end of the delivery device).

FIG. 4C illustrates a tube 48 embodiment implanted within a vessel, wherein the tube incorporates a pair of leaflets 51 to selectively modify blood flow through the vessel. The tube 48 and the leaflets 51 can be formed with a variety of materials, and are preferably formed with a flexible and/or stretchable material so as to avoid their damaging during the deployment procedure. As before, the deployment members 41 are releasably engaged with the hooks 45, and can be adapted to disengage from the hooks when pulled in the direction of the arrow. Once the valve 48 is separated from the rest of the apparatus 40, the catheter 42 and deployment members 41 can be retracted to leave the valve 48 fully deployed in the vessel. In operation, the leaflets 51 facilitate valve function by selectively allowing blood flow in a first direction, and selectively restricting blood flow in a second direction opposite the first direction. In particular, the leaflets 51 move outwardly to open the valve when subjected to blood flow in the direction opposite the arrow, and move inwardly to close the valve when subjected to blood flow in the direction of the arrow. As illustrated, the valve 48 is designed to facilitate net blood flow in the direction opposite the arrow.

Figure 5A:
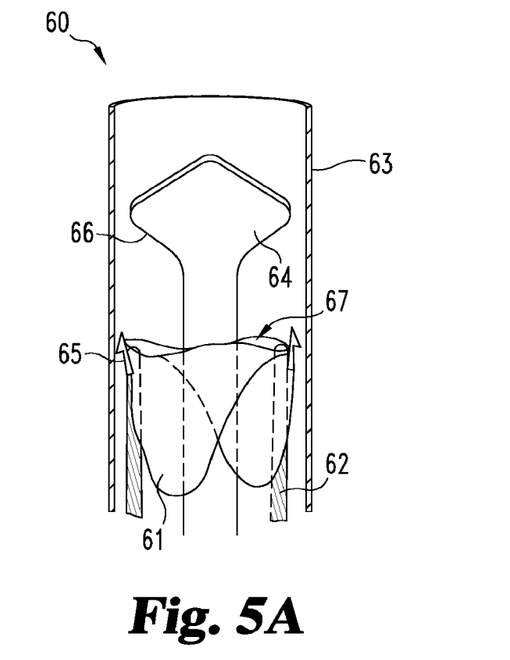
FIGS. 5A and 5B provide perspective views of an apparatus of the present invention, which includes a deflecting element.
Figure 5B:
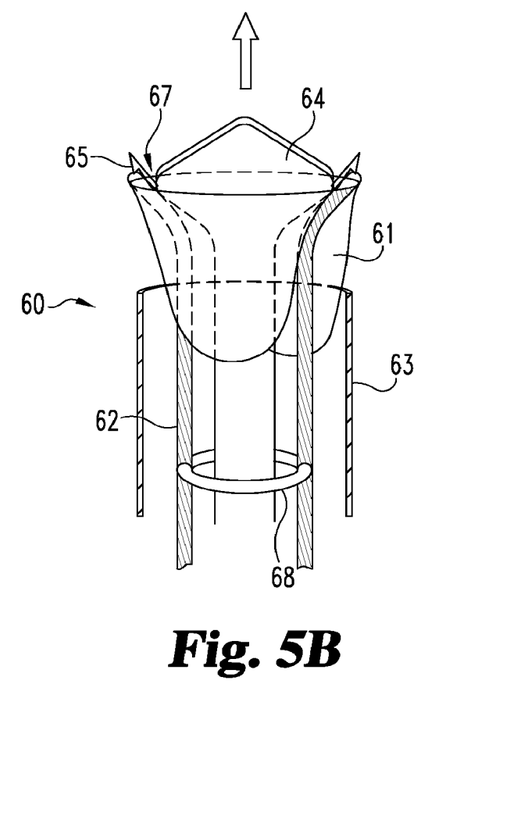

With reference now to FIGS. 5A and 5B together, shown in FIG. 5A is another apparatus 60 of the present invention for deploying an artificial implant device 61 within a vascular vessel. The apparatus 60 includes two flexible deployment members 62 slidably received within a delivery catheter 63. Further slidably received within the catheter 63 is a deflecting element 64 configured to deflect the distal ends of the deployment members 62 toward the vessel walls during deployment of the artificial implant device 61. The artificial implant device 61 incorporates a pair of vessel-engaging adaptations 65 for securing the artificial implant device to the vessel walls, wherein each adaptation 65 is releasably engaged with a corresponding deployment member 62.

Various deflecting element 64 configurations can be designed through routine experimentation so as to allow for optimal placement of the vessel-engaging adaptations 65 within the vessel. For example, the deflecting element 64 can include an angled portion 66 adapted to suitably direct the distal ends of the deployment members 62 toward the vessel walls when the deployment members are sufficiently moved in the direction of the arrow. As shown in FIG. 5B, when the flexible deployment members 62 contact the angled portion 66, the angled portion deflects the distal ends of the deployment members 62 away from the center of the lumen. In FIG. 5B, the deflecting element 64 protrudes slightly from the distal end of the catheter 63 to provide a path through which the deployment members 62 can pass upon exiting the catheter. In operation, the deployment members 62 are pushed generally in the direction of the arrow until the vessel-engaging adaptations 65 penetrate or embed within the vessel walls to anchor the artificial implant device 61 within the vessel. The illustrative artificial implant device 61 comprises a bi-leaflet valve, which includes an opening 67 through which the deflecting element 64 can pass during deployment. The opening 67 permits the deflecting element 64 to pass through the valve 61 without damaging the same.

Certain embodiments provide deployment members connected to each other and/or a delivery device. Similarly, other embodiments provide a deflecting element connected to one or more deployment members and/or a delivery device. In still other embodiments, a stabilization element is incorporated into one or more deployment members and/or a deflecting element to provide greater control over the placement of the anchoring elements during deployment. For example and as illustrated in FIG. 5B, apparatus 60 can include a stabilization ring 68 (or other similar device) attachable to the deployment members 62 to provide proper spacing of the deployment members during implantation of the valve 61. In other embodiments, one or more deployment members are configured to slide along a stabilization track within a delivery device.

Figure 6A:
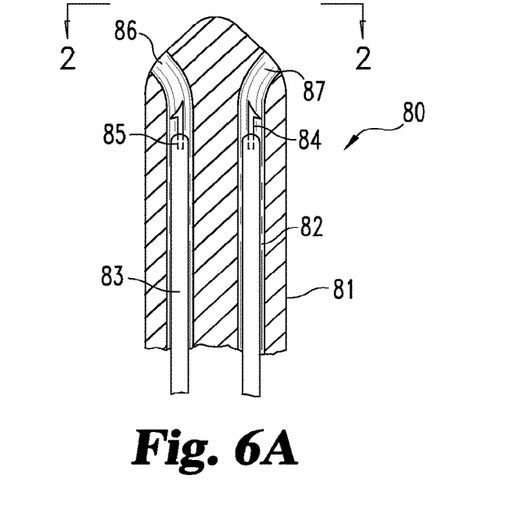
FIG. 6A provides a front view of another apparatus of the present invention.
Figure 6B:
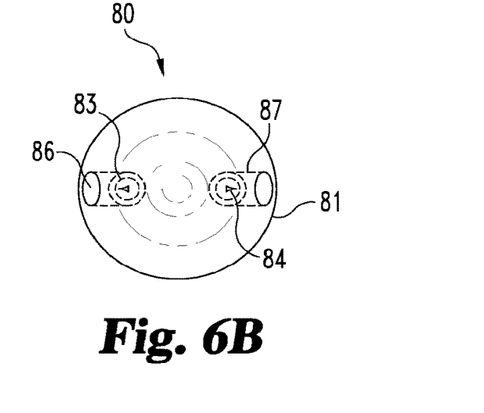
FIG. 6B provides a cross-sectional view of the apparatus of FIG. 6A along the view line 2-2 shown in FIG. 6A.

With reference now to FIGS. 6A and 6B together, shown in FIG. 6A is another deployment apparatus 80 of the present invention. The apparatus 80 comprises a delivery device 81, which includes a pair of passageways 82 therethrough. Slidably received within the passageways 82 are corresponding flexible deployment members 83, wherein the deployment members are releasably engaged with corresponding anchoring elements 84. In the illustrated embodiment, the distal tips of the deployment members 83 include corresponding slots 85 into which portions of the anchoring elements 84 are releasably inserted, for example, by force fitting.

Figure 6C:
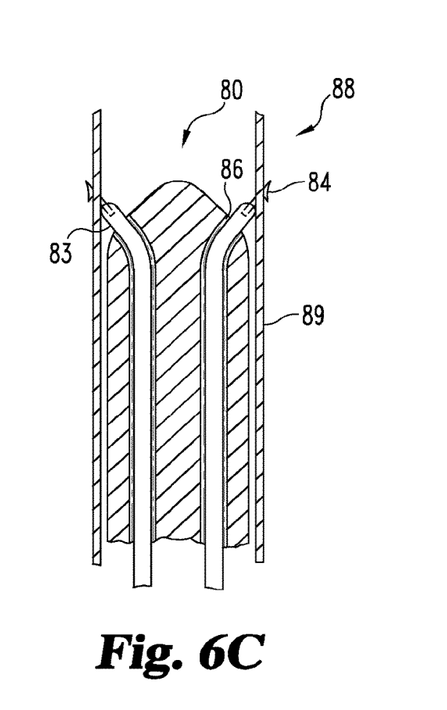
FIG. 6C provides an illustration of the apparatus of FIG. 6A being used to deploy anchoring elements within walls of a vascular vessel.

The deployment members 83 are configured to slide back and forth within the passageways 82, and to protrude through openings 86 in the passageways (e.g., as shown in FIG. 6C) when advanced far enough distally. The distal portions of the passageways 82 include angled portions 87 to suitably guide the deployment members 83 away from each other and toward the vessel walls. In this regard, a variety of passageway 82 and passageway opening 86 sizes, shapes, and configurations can be designed through routine experimentation so as to allow for optimal placement of the anchoring elements 84 within the vessel. FIG. 6B provides a top, sectional view of apparatus 80, along the view line 2-2 shown in FIG. 6A. This illustration generally shows the deployment members 83 proximal of the angled portions 87 within the passageways 82.

Figure 6D:
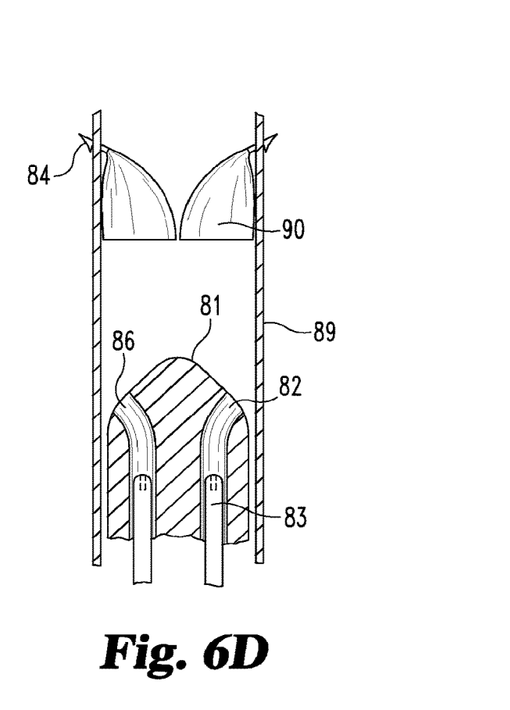
FIG. 6D illustrates anchoring elements deployed in walls of a vascular vessel, wherein the anchoring elements are attached to an artificial device.

FIGS. 6C and 6D show an illustrative deployment of anchoring elements 84 in a body vessel 88 using apparatus 80, wherein FIG. 6C depicts the flexible deployment members 83 protruding through the openings 86, and forcing the anchoring elements 84 to engage with walls 89 of the vessel 88. Shown in FIG. 6D are anchoring elements 84 deployed within bodily vessel 88. The anchoring elements 84 are attached to an artificial implant device 90, wherein the artificial implant device and method of attaching the same to anchoring elements 84 can comprise any of those herein disclosed. In certain embodiments, the artificial implant device 90 is percutaneously attached to the anchoring elements 84 during or following deployment of the anchoring elements. In other embodiments, at least a portion of an artificial implant device is receivable concentrically around a delivery device or within one or more delivery device passageways prior to deployment of the anchoring elements.

Figure 7A:
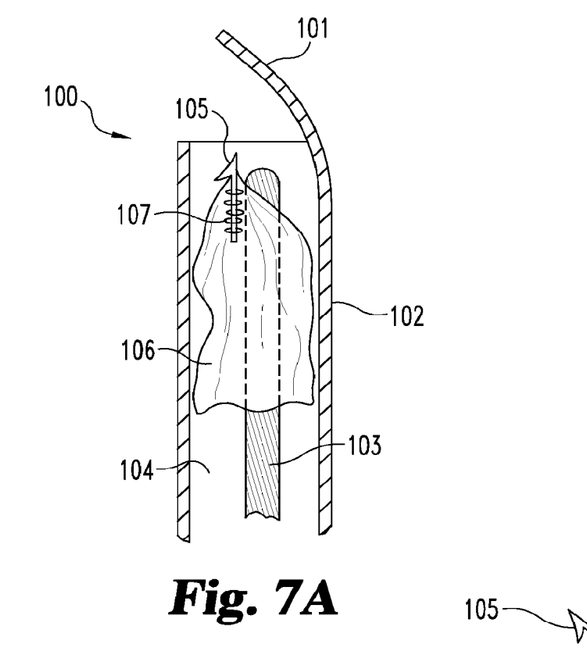
FIGS. 7A and 7B provide front views of another apparatus of the present invention.
Figure 7B:
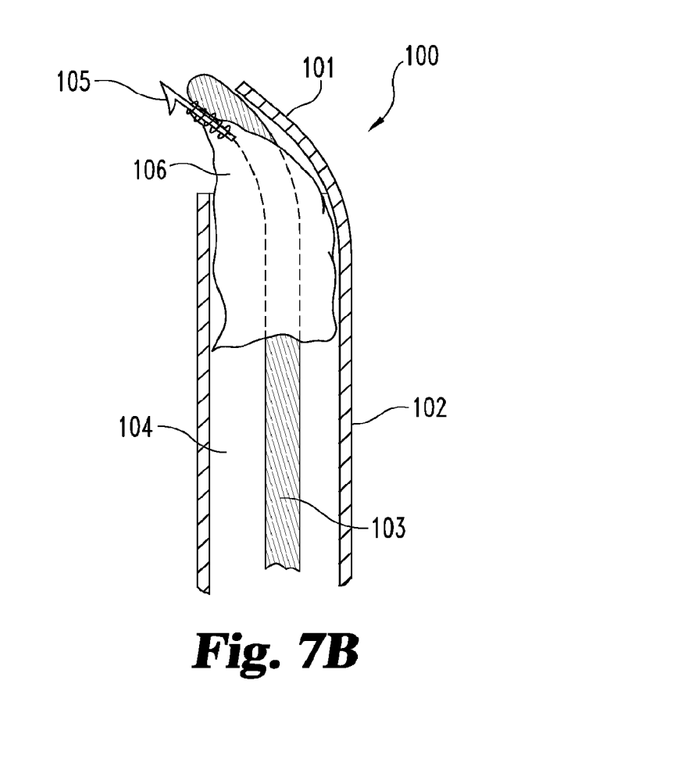

FIGS. 7A and 7B provide another apparatus 100 of the present invention, wherein the apparatus includes a deflecting element 101 incorporated into a delivery device 102. Also included is a single deployment member 103 receivable within a lumen 104 of the delivery device 102. The apparatus 100 is configured to deploy an anchoring element 105 within a vascular vessel, wherein the anchoring element 105 is releasably engaged with the deployment member 103 via a releasable bonding agent 106. An artificial implant device 107 is connected to the anchoring element 105 with sutures 108.

Figure 8A:
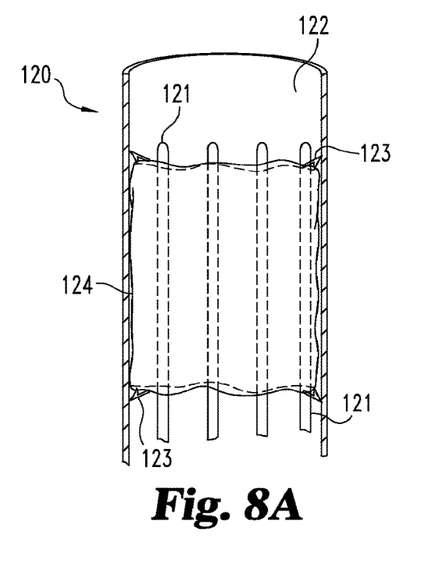
FIG. 8A provides a front view of another inventive apparatus being used to deploy a medical implant within a vascular vessel.
Figure 8B:
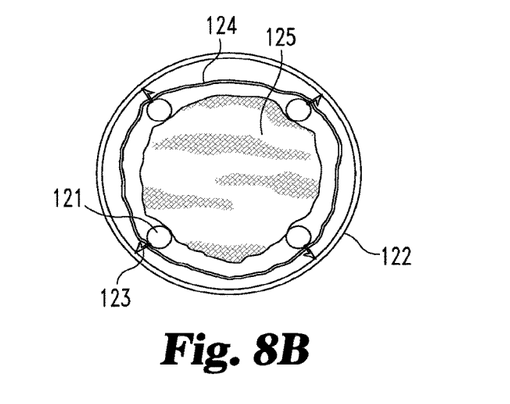
FIG. 8B provides a cross-sectional view of the apparatus of FIG. 8A along the view line 2-2 shown in FIG. 8A.

With reference now to FIGS. 8A through 8D, shown in FIG. 8A is another inventive apparatus 120 useful for deploying an implant device within a vascular vessel. The apparatus 120 generally includes a plurality of elongate deployment members 121 which are slidably received within the lumen of an endoluminally-advanceable delivery device 122. Each of the deployment members is releasably engaged with at least one anchoring element 123 for example as described elsewhere herein. The anchoring elements are attached to or incorporated into the implant, which in this particular instance, includes a tubular body 124. While the deployment member are engaged with the anchoring elements through walls of the implant 124 in this particular embodiment, in alternative forms, the implant 124 will separate and fully prevent the anchoring elements and deployment members from contacting one another. The anchoring elements are configured to attach the implant to a vessel wall. FIG. 8B provides a cross-sectional view of apparatus 120, and shows that the deployment members are affixed to and positioned around an expandable member 125 (e.g., a balloon). While not necessary to broader aspects of the invention, the deployment members are spaced essentially equidistant from one another around member 125.

Figure 8C:
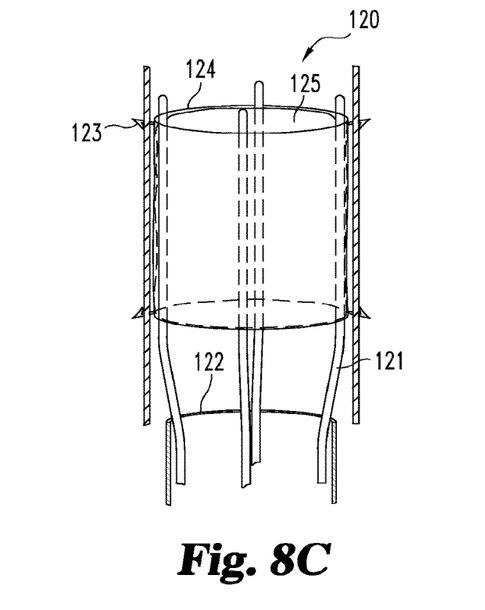
FIG. 8C shows the apparatus of FIG. 8A at a further stage of deploying the medical implant within the vascular vessel.
Figure 8D:
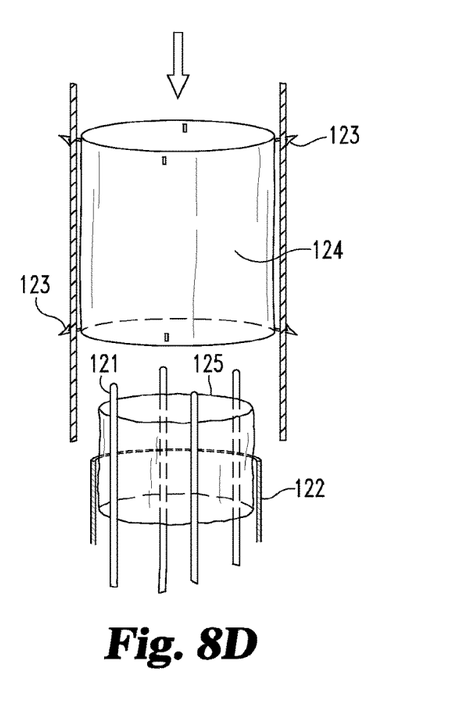
FIG. 8D shows the apparatus of FIG. 8A at still a further stage of deploying the medical implant within the vascular vessel.

FIG. 8C shows apparatus 120 within a vascular vessel after the implant 124 and corresponding portions of the deployment members 121 and expandable member 125 have been deployed from the distal end of the delivery device 122. At this particular stage of delivery, the expandable member 125 has been expanded to forcibly contact inner regions of the deployment members 121 (and potentially also contact interior surfaces of tubular body 124) so as to force such elements laterally outward which in turn forces the anchoring elements 123 toward and into the vessel wall 130 as shown. Optionally, distal regions of the deployment member 121 can be shaped and configured as described elsewhere herein, for example, to bend in an outward direction upon exiting the distal end of the delivery device 122 as shown for further assisting and guiding the anchoring elements toward the vessel wall. FIG. 8D shows the apparatus at another stage of deployment. Here, the expandable member 125 has been deflated and retracted back into the delivery device along with the deployment members. With these retractions, the implant 124 and/or the anchoring elements have disengaged from the deployment members and/or the expandable member so as to remain deployed in the vascular vessel. Implant 124 could be or form part of a number of implantable devices including but not limited to valves, stents, filter and occluders.

The remodelable material of the present invention (e.g., the material used to form the tube 48 of FIG. 4A) can be formed with a generally biocompatible and remodelable extracellular matrix material. Suitable ECM material of the present invention can be derived from a variety of natural sources, including pericardial tissues (e.g., pericardial sacs), amniotic sacs, connective tissues, bypass grafts, skin patches, blood vessels, cartilage, dura mater, skin, fascia, umbilical tissues, renal capsule membrane, serosa, peritoneum, basement membrane materials (e.g., liver basement membrane), submucosa and the like. Remodelable materials are derived from a particular animal species, typically mammalian, such as human, bovine, equine, ovine, or porcine. These materials may include a portion of an organ or structural tissue components of an organ. Moreover, suitable remodelable tissues include xenografts (i.e., cross species, such as a non-human donor for a human recipient), allografts (i.e., interspecies with a donor of the same species as the recipient) and autografts (i.e., the donor and the recipient being the same individual). Suitable remodelable tissue is generally soft tissue. In certain embodiments, the remodelable material is fully or partially crosslinked as discussed in detail below.

The submucosal tissue of cattle, sheep, and other warm-blooded vertebrates, especially pigs, provides a particularly preferred material for use in the present invention. A favorable characteristic of remodelable submucosal tissue (e.g., small intestinal submucosa, stomach submucosa, urinary bladder submucosa, or uterine submucosa) is that it has the capacity to induce host tissue proliferation and lead to the remodeling and regeneration of tissue structures upon in vivo implantation.

Submucosal tissue may, for example, be prepared as described in U.S. Pat. Nos. 4,902,508; 5,554,389; and 6,206,931. Again, it should be understood that submucosa can be derived from any suitable organ or other biological structure, including for example, submucosa derived from the alimentary, respiratory, intestinal, urinary or genital tracts of warm-blooded vertebrates. Submucosa useful in the present invention can be obtained by harvesting such tissue sources and delaminating the submucosa from smooth muscle layers, mucosal layers, and/or other layers occurring in the tissue source. Thereafter, the submucosa can be assembled into tissue segments (e.g., sheets, strands, and other shapes) or stored for later processing.

An artificial implant device of the invention may also be derived from a number of biological polymers, which can be naturally occurring or the product of in vitro fermentation, recombinant genetic engineering, and the like. Purified biological polymers can be appropriately formed into a substrate by techniques such as weaving, knitting, casting, molding, and extrusion. Suitable biological polymers include, without limitation, collagen, elastin, keratin, gelatin, polyamino acids, polysaccharides (e.g., cellulose and starch) and copolymers thereof.

The remodelable ECM material may be manipulated before or after it is assembled into a component of the present invention. For example, the material may be cut, trimmed, sterilized, and/or treated with one or more property modifiers. In certain embodiments, the ECM material is crosslinked before or after any preliminary processing and/or storage. Crosslinking tends to fix ECM material in the shape imposed during the crosslinking process. However, because certain crosslinking agents and/or certain degrees of crosslinking can destroy the remodelable properties of a remodelable material, where preservation of remodelable properties is desired, any crosslinking of the remodelable ECM material can be performed to an extent or in a fashion that allows the material to retain at least a portion of its remodelable properties. Following any crosslinking, the material can be further processed, which can involve additional chemical and/or mechanical manipulation of the material, as well as processing the material into the desired invention component.

Crosslinking, in addition to providing mechanical stabilization (e.g., by anchoring the collagen fibrils and preventing enzymatic degradation of the tissue), can decrease or eliminate antigens in the tissue. Glutaraldehyde, formaldehyde or a combination thereof is typically used for fixation, but other fixatives can be used, such as epoxides, epoxyamines, diimides and other difunctional/polyfunctional aldehydes. In particular, aldehyde functional groups are highly reactive with amine groups in proteins, such as collagen. Epoxyamines are molecules that generally include both an amine moiety (e.g. a primary, secondary, tertiary, or quaternary amine) and an epoxide moiety. The epoxyamine compound can be a monoepoxyamine compound and/or a polyepoxyamine compound.

In addition to being crosslinked, the material can be treated (e.g., brought into contact, impregnated, coated, etc.) with one or more desirable compositions, such as anticoagulants (e.g., heparin), growth factors, other desirable property modifiers, and the like to modify the tissue properties. Specifically, the tissue can be treated with an anticalcification agent to reduce calcification of the tissue following implantation and/or to encourage remodeling of the tissue material. Generally, any calcification reducing agents would be contacted with the composite matrix following crosslinking, although some calcification reducing agents can be contacted with the tissue prior to crosslinking. Suitable calcification reducing agents include, for example, alcohols, such as ethanol and propylene glycol, detergents (e.g., sodium dodecyl sulfate), toluidine blue, diphosphonates, and multivalent cations, especially Al$^{+3}$, Mg$^{+2}$ or Fe$^{+3}$, or corresponding metals that can oxidize to form the multivalent metal cations.

Additionally, to encourage ingrowth of viable cells, the tissue can be treated to reduce or eliminate toxicity associated with aldehyde crosslinking and/or associated with compounds that stimulate the infiltration of the tissue by desirable cells. Further, the tissue can be crosslinked with dialdehydes or the like to reduce or eliminate any cytotoxicity. Suitable compounds for reduction of aldehyde cytotoxicity include, for example, amines, such as amino acids, ammonia/ammonium, sulfates, such as thiosulfates and bisulfates, surfactants and combinations thereof.

As prepared, the ECM material may optionally retain various bioactive components native to the source tissue. For example, the ECM material may include one or more growth factors, such as basic fibroblast growth factor (FGF-2), transforming growth factor beta (TGF-beta), epidermal growth factor (EGF), and/or platelet derived growth factor (PDGF). Further, the submucosa or other ECM material of the present invention may include other biological materials, such as heparin, heparin sulfate, hyaluronic acid, fibronectin and the like. Thus, generally speaking, the ECM material may include a bioactive component that induces, directly or indirectly, a cellular response, such as a change in cell morphology, proliferation, growth, protein or gene expression, which again, is desirable for promoting tissue ingrowth into one of the components of the present invention.

In addition to, or as an alternative to, the inclusion of such native bioactive components, non-native bioactive components, such as those synthetically produced by recombinant technology or other methods, may be incorporated into the ECM material. The addition of a non-native component, e.g., a growth factor, with a tissue matrix may involve direct attachment, application of a coating, including an adhesive or binder, or chemical binding, involving a binding agent.

The ECM material used in the invention is preferably highly purified, for example as described in U.S. Pat. No. 6,206,931. Thus, the preferred material will exhibit an endotoxin level of less than about 12 endotoxin units (EU) per gram, more preferably less than about 5 EU per gram, and most preferably less than about 1 EU per gram. As additional preferences, the ECM material may have a bioburden of less than about 1 colony forming units (CFU) per gram, and more preferably less than about 0.5 CFU per gram. Fungus levels are desirably low as well, for example less than about 1 CFU per gram, and more preferably less than about 0.5 CFU per gram. Nucleic acid levels are preferably less than about 5 μg/mg, and more preferably less than about 2 μg/mg, while virus levels are preferably less than about 50 plate forming units (PFU) per gram, and more preferably less than about 5 PFU per gram. These and additional properties of submucosa taught in U.S. Pat. No. 6,206,931 may be characteristic of the ECM material used in the present invention.

A variety of synthetic polymeric materials may be utilized in the present invention (e.g., to form the tube 124 of FIG. 8A). The synthetic polymeric material can be either a bioresorbable and/or non-bioresorbable plastic. Bioresorbable, or bioabsorbable polymers that could be used include, but are not limited to, poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyhydroxyalkanaates, polyphosphoester, polyphosphoester urethane, poly(amino acids), cyanoacrylates, poly(trimethylene carbonate), poly(iminocarbonate), copoly(ether-esters) (e.g., PEO/PLA), polyalkylene oxalates, and polyphosphazenes.

Non-bioresorbable, or biostable polymers that could be used include, but are not limited to, polytetrafluoroethylene (PTFE) (including expanded PTFE) and/or polyethylene terephthalate (PET), polyurethanes, silicones, and polyesters and other polymers such as, but not limited to, polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins, polycarbonates; polyoxymethylenes; polyimides; polyethers; epoxy resins, polyurethanes; rayon; and rayon-triacetate. The material may be in the form of yarns, fibers, and/or resins, monofilament yarns, high tenacity polyester. Further, the present application contemplates other plastic, resin, polymer, woven, and fabric surgical materials, other conventional synthetic surgical materials, such as a shape-memory plastic, and/or combinations of such materials.

All publications and patent applications cited in this specification are herein incorporated by reference as if each individual publication or patent application were specifically and individually indicated to be incorporated by reference. Further, any theory, mechanism of operation, proof, or finding stated herein is meant to further enhance understanding of the present invention, and is not intended to limit the present invention in any way to such theory, mechanism of operation, proof, or finding. While the invention has been illustrated and described in detail in the drawings and foregoing description, the same is to be considered as illustrative and not restrictive in character, it being understood that only selected embodiments have been shown and described and that all equivalents, changes, and modifications that come within the spirit of the inventions as defined herein or by the following claims are desired to be protected.

What is claimed is:

1. An apparatus for modifying blood flow within a vascular vessel, comprising:
   a delivery device having a lumen;
   at least one elongate deployment member slidably received within said lumen;
   an artificial implant device comprising a valve and having at least one anchoring element for anchoring the artificial implant device to walls of the vessel, said at least one anchoring element releasably and directly engaged with said at least one elongate deployment member;
   a deflecting element slidably received in the delivery device independent of the at least one elongate deployment member, the deflecting element having a distal region presenting an angled portion positionable distally of a distal end of the delivery device; and
   wherein a lateral surface of the at least one elongate deployment member is movable against and along a surface of the angled portion of the deflecting element so as to deflect the at least one elongate deployment member and the at least one anchoring element toward a wall of the vascular vessel.

2. The apparatus of claim 1, wherein the at least one anchoring element comprises a barb.

3. The apparatus of claim 1, wherein said at least one elongate deployment member includes a plurality of elongate deployment members and wherein said at least one anchoring element includes a plurality of anchoring elements each releasably engaged with a corresponding one of said elongate deployment members.

4. The apparatus of claim 1, wherein said at least one anchoring element is configured to disengage from said at least one elongate deployment member when sufficient force is applied to separate the deployment member from the anchoring element.

5. The apparatus of claim 1, wherein said artificial implant device comprises a flexible material.

6. The apparatus of claim 1, wherein at least a portion of said artificial implant device is receivable within said delivery device.

7. The apparatus of claim 1, wherein said at least one elongate deployment member is configured to receive a portion of said at least one anchoring element.

8. The apparatus of claim 1, wherein said at least one elongate deployment member is configured to receive at least a portion of said artificial implant device.

9. The apparatus of claim 1, wherein said at least one elongate deployment member has an end that is curved.

10. An apparatus for modifying blood flow within a vascular vessel, comprising:
   a delivery device having at least one deployment member passageway therethrough;
   at least one deployment member slidably received within said at least one passageway;
   at least one anchoring element releasably and directly engaged with said at least one deployment member;
   at least one valve leaflet attachable to said at least one anchoring element a deflecting element slidably received in the delivery device, the deflecting element having a distal region slidably positionable distally of a distal end of said delivery device and distally of said at least one anchoring element releasably engaged with said at least one deployment member; and
   wherein said distal region is configured to deflect said at least one deployment member toward a wall of the vascular vessel upon movement of said at least one deployment member against said distal region.

11. The apparatus of claim 10, wherein said distal region presents an angled portion, and wherein a lateral surface of the at least one deployment member is movable against and along a surface of the angled portion so as to deflect the at least one elongate deployment member toward the wall of the vascular vessel.

12. The apparatus of claim 10, wherein the at least one anchoring element comprises a barb.

13. An apparatus for deploying an artificial implant device within a vascular vessel, comprising:
   a delivery device having a lumen;
   at least one elongate member slidably received within said lumen;
   an artificial implant device comprising a valve and having at least one barb for anchoring the artificial implant device to a wall of the vessel, the at least one barb releasably and directly engaged with the at least one elongate member; and
   an elongate element slidably received in the delivery device, the elongate element having a distal region presenting an angled portion positionable distally of a distal end of the delivery device; and
   wherein a lateral surface of the at least one elongate member is movable against and along a surface of the angled portion when the angled portion is positioned distally of the distal end of the delivery device, so as to deflect the at least one elongate member and thereby the at least one barb toward a wall of the vascular vessel.

14. The apparatus of claim 13, wherein the at least one elongate member includes a plurality of elongate members and wherein the at least one barb includes a plurality of barbs each releasably engaged with a corresponding one of the elongate members.

15. The apparatus of claim 13, wherein the at least one barb is configured to disengage from the at least one elongate member when sufficient force is applied to separate the elongate member from the barb.

16. The apparatus of claim 13, wherein the artificial implant device comprises a flexible material.

17. The apparatus of claim 13, wherein at least a portion of said artificial implant device is receivable within said delivery device.

18. The apparatus of claim 13, wherein said at least one elongate member is configured to receive a portion of said at least one barb.

19. The apparatus of claim 13, wherein said at least one elongate member is configured to receive at least a portion of said artificial implant device.

* * * * *